(12) United States Patent
Xiao et al.

(10) Patent No.: US 8,940,648 B2
(45) Date of Patent: Jan. 27, 2015

(54) PROCESS FOR PRODUCING SILICON AND OXIDE FILMS FROM ORGANOAMINOSILANE PRECURSORS

(71) Applicant: Air Products and Chemicals, Inc., Allentown, PA (US)

(72) Inventors: Manchao Xiao, San Diego, CA (US); Xinjian Lei, Vista, CA (US); Heather Regina Bowen, Vista, CA (US); Mark Leonard O'Neill, San Marcos, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 13/964,658

(22) Filed: Aug. 12, 2013

(65) Prior Publication Data
US 2013/0330937 A1    Dec. 12, 2013

Related U.S. Application Data

(63) Continuation-in-part of application No. 11/439,554, filed on May 23, 2006, now Pat. No. 7,875,312, and a continuation of application No. 12/976,041, filed on Dec. 22, 2010, now Pat. No. 8,530,361.

(51) Int. Cl.
*H01L 21/31* (2006.01)
*H01L 21/02* (2006.01)
(Continued)

(52) U.S. Cl.
CPC .......... *H01L 21/02211* (2013.01); *C07F 7/025* (2013.01); *C23C 16/402* (2013.01);
(Continued)

(58) Field of Classification Search
None
See application file for complete search history.

(56) References Cited

U.S. PATENT DOCUMENTS 4,200,666 A    4/1980 Reinberg
(Continued)

FOREIGN PATENT DOCUMENTS

EP    0 481 706 A1    4/1992
EP    1149934    8/2005
(Continued)

OTHER PUBLICATIONS

Gary E. McGuire, Semiconductor Materials and Process Technology Handbook, Noyes Publications, NJ, 1988, pp. 239-301.
(Continued)

*Primary Examiner* — Kyoung Lee
(74) *Attorney, Agent, or Firm* — Rosaleen P. Morris-Oskanian

(57) ABSTRACT

A method for depositing a silicon containing film on a substrate using an organoaminosilane is described herein. The organoaminosilanes are represented by the formulas:

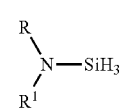

A

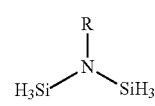

B

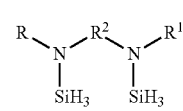

C wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_6$-$C_{10}$ aromatic group with or without substituents, a $C_3$-$C_{10}$ heterocyclic group with or without substituents, a hydrogen atom, a silyl group with substituents and wherein R and $R^1$ in formula A can be combined into a cyclic group and $R^2$ representing a single bond, $(CH_2)$, chain, a ring, $C_3$-$C_{10}$ branched alkyl, $SiR_2$, or $SiH_2$.

14 Claims, 2 Drawing Sheets

(51) Int. Cl.
- C07F 7/02 (2006.01)
- C23C 16/40 (2006.01)
- C23C 16/455 (2006.01)
- H01L 21/314 (2006.01)
- H01L 21/316 (2006.01)

(52) U.S. Cl.
CPC .... *C23C16/45553* (2013.01); *H01L 21/02164* (2013.01); *H01L 21/02219* (2013.01); *H01L 21/02222* (2013.01); *H01L 21/02271* (2013.01); *H01L 21/0228* (2013.01); *H01L 21/3145* (2013.01); *H01L 21/31608* (2013.01); *H01L 21/31633* (2013.01)
USPC ........... 438/781; 438/739; 438/784; 438/793; 438/794

(56) References Cited

U.S. PATENT DOCUMENTS

| | | | |
|---|---|---|---|
| 5,008,422 | A | 4/1991 | Blum et al. |
| 5,234,869 | A | 8/1993 | Mikata et al. |
| 5,250,473 | A | 10/1993 | Smits |
| 5,382,550 | A | 1/1995 | Iyer |
| 5,458,689 | A | 10/1995 | Saito |
| 5,622,784 | A * | 4/1997 | Okaue et al. ............... 428/447 |
| 5,656,076 | A | 8/1997 | Kikkawa |
| 5,772,757 | A | 6/1998 | Saito |
| 5,837,056 | A | 11/1998 | Kikkawa |
| 5,874,368 | A | 2/1999 | Laxman et al. |
| 5,976,991 | A | 11/1999 | Laxman et al. |
| 6,153,261 | A | 11/2000 | Xia et al. |
| 6,391,803 | B1 | 5/2002 | Kim et al. |
| 6,486,015 | B1 | 11/2002 | Chaudhary et al. |
| 6,500,772 | B2 | 12/2002 | Chakravarti et al. |
| 6,630,413 | B2 | 10/2003 | Todd |
| 6,963,006 | B2 | 11/2005 | Tsui et al. |
| 6,974,780 | B2 | 12/2005 | Schuegraf |
| 7,098,150 | B2 | 8/2006 | Misra et al. |
| 7,482,286 | B2 | 1/2009 | Misra et al. |
| 2002/0175393 | A1 | 11/2002 | Baum et al. |
| 2005/0163927 | A1 | 7/2005 | McSwiney et al. |
| 2006/0051975 | A1 | 3/2006 | Misra et al. |
| 2006/0099831 | A1 | 5/2006 | Borovik et al. |
| 2006/0258173 | A1 | 11/2006 | Xiao et al. |
| 2007/0275166 | A1 | 11/2007 | Thridandam et al. |
| 2009/0069588 | A1 | 3/2009 | Xiao et al. |
| 2009/0075490 | A1 | 3/2009 | Dussarrat |

FOREIGN PATENT DOCUMENTS

| | | |
|---|---|---|
| GB | 1123252 | 8/1968 |
| JP | 6132276 | 5/1994 |
| JP | 06132284 | 5/1994 |
| JP | 07235535 | 9/1995 |
| JP | 00195801 | 7/2000 |
| JP | 2001156063 | 6/2001 |
| JP | 200526244 | 1/2005 |
| KR | 1020050018641 | 2/2005 |
| KR | 1020060018641 | 2/2006 |
| WO | 0265508 | 8/2002 |
| WO | 2004010467 | 1/2004 |
| WO | 2004017383 | 2/2004 |
| WO | 2004030071 | 4/2004 |
| WO | 2005080628 | 9/2005 |
| WO | 2005093126 | 10/2005 |
| WO | 2006033699 | 3/2006 |
| WO | 2006036538 | 4/2006 |
| WO | 2006097525 | 9/2006 |

OTHER PUBLICATIONS

Stanley Wolf, Silicon Processing for the VLSI Era, Lattice Press, CA 1990, pp. 327-330.
Arthur K. Hochberg, et al, Diethylsilane as a Source for the Deposition . . . , Mat. Res. Soc, Symp. Proc., vol. 204, 1991, pp. 509-513.
Tetsuji Sorita, et al, Mass Spectrometric and Kinetic Study of Low-Pressure . . . , J. Elec. Soc., vol. 141, No. 12, 1994, pp. 3506-3511.
B.J. Aylett, et al, The Preparation and Properties of Dimethylamino- and . . . , J. Chem. Soc. (A), 1967, pp. 652-655.
Sei Sujishi, et al, Effect of Replacement of Carbon by Silicon in Trimethylamine . . . , J. Am. Chem. Soc., vol. 78, 1956, pp. 4631-4636.
Kenneth Hedberg, The Molecular Structure of Trisilylamine (SiH3) 3N1, 2, J. Am. Chem. Soc., 1955, vol. 77, pp. 6491-6492.
J.M. Grow, et al, Growth Kinetics and Characterization of Low Pressure . . . , Mat. Letters vol. 23, 1995, pp. 187-193.
B.A. Scott, et al, Preparation of Silicon Nitride with Good Interface . . . , Chemtronics, 1989, vol. 4, pp. 230-233.
B.J. Aylett, et al, Silicon-Nitrogen Compounds. Part V. Diphenylamino-derivatives of Silane, J. Chem. Soc., 1989, 636-639.
Norbert W. Mizel, Simple Silylhydrazines as Models for Si-N.beta.-donor Interactions in SINN Units, Chemistry-A European Journal, 1998, 692-698.
Hubert Schmidbuar, et al, Differences in Reactivity of 1,4-Disilabutane and N-Tetrasilane Towards Secondary Amines, Zeitschrift Fur Naturforschung B: Chemical Sciences, 1990, 1679-1683.
A.V. Golubinszkij, et al, Molecular-structure Examination of Some Organic Silicon Compounds by Electron Diffraction, Kemiai Kozlemenyek, 46, 1976, 473-480.
C. Glidewell, et al, Electron Diffraction Determination of the Molecular Structure of Tetrasilylhydrazine, Journal of the Chemical Society, 1970, 318-320.
H. Beck, et al, Radical Ions. 36. Structural Changes Accompanying the One-Electron Oxidation of Hydrazine and Its Silyl Derivatives1-3, Journal of the American Chemical Society, 1980, 4421-4428.
B.J. Aylett, the Silyl Group as an Electron Acceptor, J. Inorg. Nucl. Chem., 1956, 325-329.
N. Bingo, et al, Correlations Among X-H Bond Lengths, X-H Stretching Frequencies, and Bond Order Matrix Elements P Hx: where X=C, N, and Si, J. Sci. Hiroshima Univ., 1976, 317-326.
B.J. Aylett, Vibrational spectra and structure of tetrasilylhydrazine and tetrasilylhydrazine-d, Spectrochimica Acta, 1960, 747-758.
C. Glidewell, et al, Some Preparative and Spectroscopic Studies of Silylamines, Journal of the Chemical Society a Inorg. Phys. Theor., 1970, 279-286.
B.J. Aylett, et al, N-Silyl Derivatives of Cyclic Secondary Amines, J. Chem. Soc, 1967, 1918-1921.
B.J. Aylett, et al, Silicon-Nitrogen Compounds. Part VIII. Base-Promoted Disproportionation of N-Methly- and N-Phenyl-Disilazane, J. Chem. Soc., 1969, 1788-1792.
D. Anderson, et al, Isopropyldisilylamine and Disilyl-t-butylamine: Preparation, Spectroscopic Properties, and Molecular Structure in the Gas Phase, determined by Electron Diffraction, J. Chem. Soc., 1989, 779-783.
Paprotta, S.; "Untersuchung von Silizium—und Germanium-Nano-Clustern fuer die moderne Speichertechnologie"; Dissertation Universitaet Hannover; Jan. 1, 2005; pp. 1-34.
V. Passarelli, Aminolysis of the Si-Cl bond and ligand exchange reaction between silicon amido derivatives and SiCl4: synthetic applications and kinetic investigations, The Royal Society of Chemistry, 2003, 413-419.
T. Shibata, et al, "ALD-SiO2 Deposition and CD Slimming Techniques for Double Patterning and a Heater-less Batch Tool", Semiconductor Manufacturing (ISSM), 2010 International Symposium, 1-3.

\* cited by examiner

PROCESS FOR PRODUCING SILICON AND OXIDE FILMS FROM ORGANOAMINOSILANE PRECURSORS

CROSS REFERENCE TO RELATED APPLICATION

The present patent application is a continuation-in-part of U.S. patent application Ser. No. 11/439,554 filed May 23, 2006 now issued U.S. Pat. No. 7,875,312 and is a continuation of U.S. patent application Ser. No. 12/976,041 filed Dec. 22, 2010.

BACKGROUND OF THE INVENTION

In the fabrication of semiconductor devices, a thin passive layer of a chemically inert dielectric material such as a silicon-containing film is essential. Thin layers of silicon-containing films such as silicon oxide function as insulators between polysilicon and metal layers, diffusion masks, oxidation barriers, trench isolation, intermetallic dielectric material with high dielectric breakdown voltages and passivation layers.

The following articles and patents are cited as representative of the art with respect to the synthesis of deposition processes employed in the electronics industry for producing silicon oxide films.

U.S. Pat. No. 5,250,473 discloses a method of providing a silicon dioxide layer having a substantially uniform thickness at an improved deposition rate on a substrate by means of low pressure chemical vapor deposition (LPCVD). The reactants generally comprise mixture of an oxidizing agent and a chlorosilane, wherein the chlorosilane is a monochlorosilane of the formula $R_1R_2SiHCl$ and where $R_1$ and $R_2$ represent an alkyl group. The silicon dioxide layer may be deposited on various substrates such as aluminum.

U.S. Pat. No. 5,382,550 discloses a CVD process for depositing $SiO_2$ film on a semiconductor substrate. An organosilicon compound, e.g., tetraethylorthosilicate (TEOS) or ditertiarybutylsilane is used as precursor.

U.S. Pat. No. 6,391,803 discloses a process for producing silicon nitride and silicon oxide films using ALD and employing compounds of the formula: $Si[N(CH_3)_2]_4$, $SiH[N(CH_3)_2]_3$, $SiH_2[N(CH_3)_2]_2$ or $SiH_3[N(CH_3)_2]$. Trisdimethylaminosilane (TDMAS) is preferred as a precursor.

U.S. Pat. No. 6,153,261 discloses a method for increasing the deposition rate in the formation of silicon oxide, silicon nitride and silicon oxynitride films which comprises using bistertiarybutylaminosilane (BTBAS) as a precursor reactant.

U.S. Pat. No. 6,974,780 discloses a process for depositing $SiO_2$ films on a substrate using a CVD reactor. Silicon precursors, such as TEOS, diethylsilane, tetramethylcyclo-tetraoxysilioxane, fluorotriethoxysilane and fluorotrialkoxysilane, in combination with water and hydrogen peroxide are used as reactants.

BRIEF SUMMARY OF THE INVENTION

Described herein is a method for depositing a stoichiometric or non-stoichiometric silicon and oxide containing film such as, but not limited to, a silicon oxide film, a silicon oxynitride film, a silicon oxycarbide film, or a silicon oxycarbonitride film onto at least a portion of a substrate. In one embodiment of the method described herein, a layer comprising silicon and oxide is deposited onto a substrate using a silane precursor and an oxidizing agent in a deposition chamber under conditions for generating a silicon oxide layer on the substrate. In the process described herein, an organoaminosilane having Formula A through Formula C described herein is employed as the silane precursor.

The classes of compounds employed as the precursor are generally represented by the formulas:

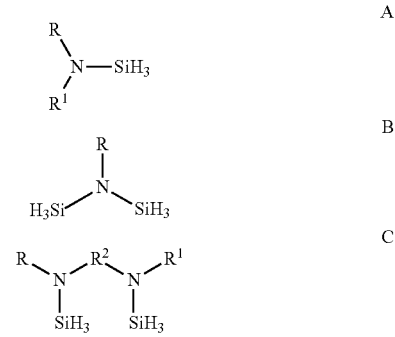

and mixtures thereof, wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a cyclic group and $R^2$ representing a single bond, $(CH_2)$, chain, a $C_3$-$C_{10}$ branched alkyl, a ring, $SiR_2$, or $SiH_2$. Preferred compounds are such that both R and $R^1$ have at least 2 carbon atoms. In one particular embodiment, the silane precursor has the formula A wherein both R and $R^1$ are isopropyl. In another particular embodiment, the organoaminosilane precursor has the formula A wherein R is n-propyl and $R^1$ is isopropyl. In yet another embodiment, the organoaminosilane precursor has the formula A wherein R is isopropyl, $R^1$ is sec-butyl and R and $R^1$ are also combined to form a heterocyclic group.

In one particular embodiment, there is provided a method for forming a silicon oxide film on a substrate comprising: reacting an oxidizing agent with a precursor comprising at least one organoaminosilane precursor selected from the group consisting of an organoaminosilane represented by the formulas:

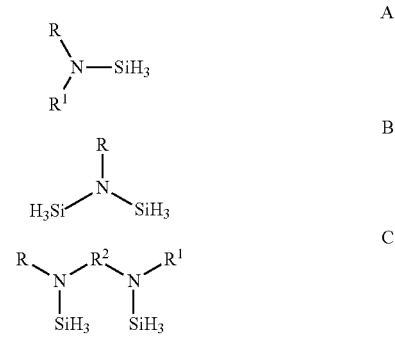

wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a heterocyclic group and $R^2$ representing a single bond, ($CH_2$), chain, a $C_3$-$C_{10}$ linear, branched, a ring, $SiR_2$, or $SiH_2$ in a vapor deposition to form the silicon oxide film on the substrate.

In another embodiment, there is provided a method for forming a silicon oxide film on a substrate comprising: forming via vapor deposition of the silicon oxide film on the substrate from a composition comprising at least one organoaminosilane precursor selected from the group consisting of an organoaminosilane represented by the formulas:

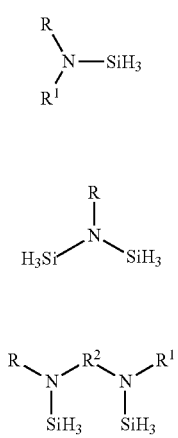

wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a heterocyclic group comprising from 2 to 6 carbon atoms and $R^2$ representing a single bond, ($CH_2$), chain, a $C_3$-$C_{10}$ linear, branched, a ring, $SiR_2$, or $SiH_2$ at least one oxidizing agent, wherein the vapor deposition is at least one selected from chemical vapor deposition, low pressure vapor deposition, plasma enhanced chemical vapor deposition, cyclic chemical vapor deposition, plasma enhanced cyclic chemical vapor deposition, atomic layer deposition or plasma enhanced atomic layer deposition.

In yet another embodiment, there is provided a method for forming a silicon oxide film on a substrate comprising: introducing an organoaminosilane represented by one of the following formulas:

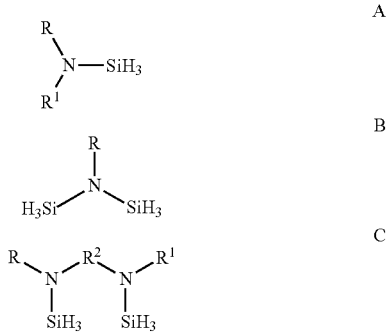

wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a heterocyclic group comprising from 2 to 6 carbon atoms and $R^2$ representing a single bond, ($CH_2$), chain, a $C_3$-$C_{10}$ linear, branched, a ring, $SiR_2$, or $SiH_2$ into a deposition chamber; introducing at least one oxidizing agent into the deposition chamber wherein the at least one oxidizing agent reacts with the organoaminosilane to provide the silicon oxide film on the substrate.

The precursors described herein when employed in CVD or ALD processes can at least one or more of the following advantages, such as, but not limited to:

an ability to facilitate formation of dielectric films at low thermal conditions such as but not limited to room temperature (e.g., 25° C.), 100° C. or less, 250° C. or less, without incurring the problems of plasma deposition;

an ability to mix the organoaminosilane having the Formula A through C described herein with other precursors, e.g., ammonia at various stoichiometries, other silicon precursors, etc., for permitting control of the ratio of Si—C, Si—N, or Si—O and thereby control the characteristics of the resulting films;

an ability to produce films having relatively high refractive indices and film stresses compared to comparative films prepared by other aminosilane precursors;

an ability to produce films having low acid etch rates compared to comparative films prepared by other aminosilane precursors;

an ability to produce films of high densities compared to comparative films prepared by other aminosilane precursors;

an ability to generate films while avoiding chlorine contamination;

an ability to operate at low pressures (20 mTorr to 2 Torr) in a manufacturable batch furnace (100 wafers or more); and, an ability to generate silicon-containing films at low temperatures, e.g., as low as 550° C. and below, or 300° C. and below, or 100° C. and below.

Figure 1A:
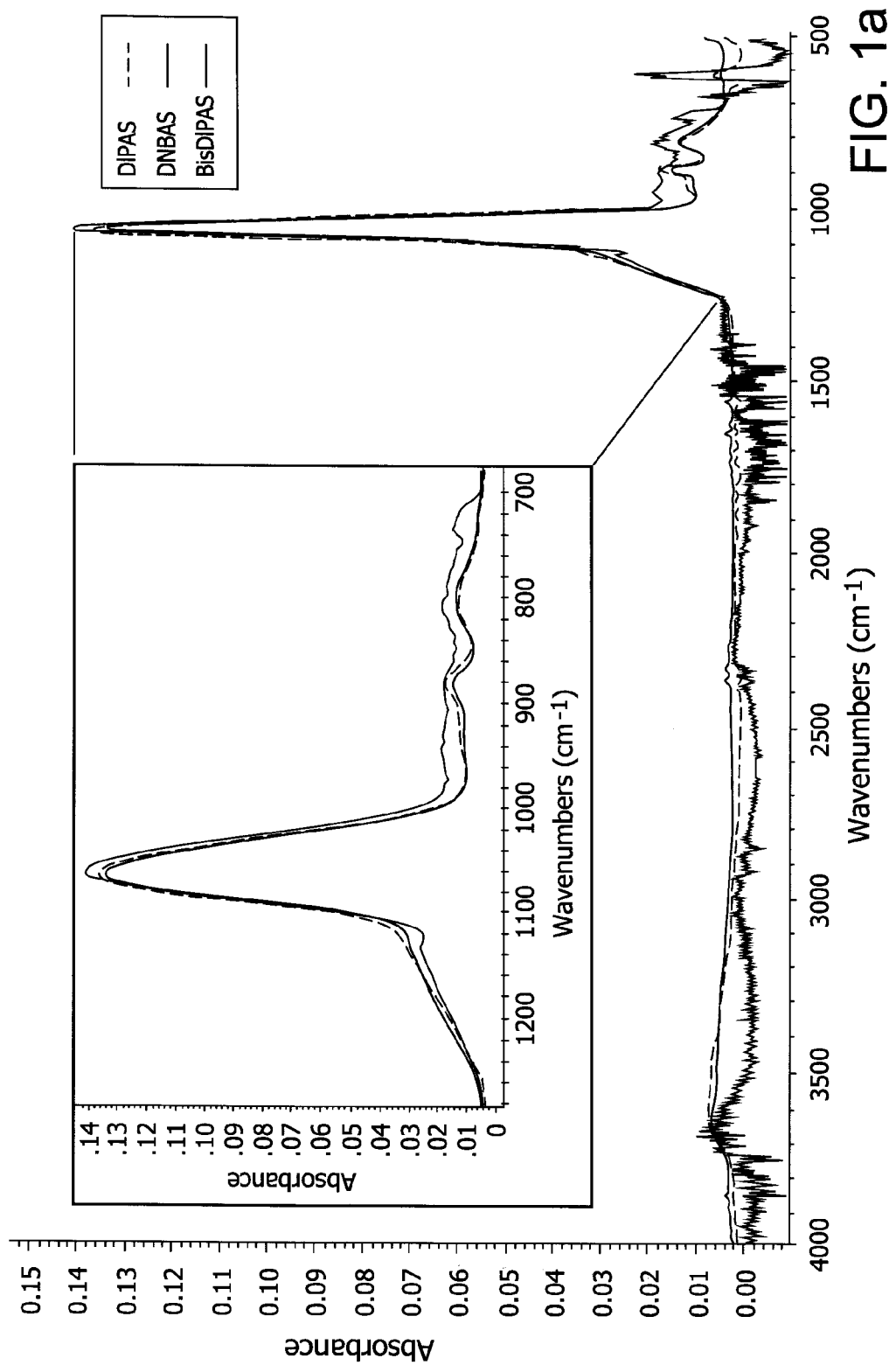
FIG. 1a and FIG. 1b provides the Fourier Transform spectroscopy spectra for silicon oxide films deposited at 150° C.

and 300° C., respectively, from the organoaminosilane precursors diisopropylaminosilane, bis(di-isopropylamino)silane and di-n-butylaminosilane.

DETAILED DESCRIPTION OF THE INVENTION

The formation of silicon oxide films on semiconductor substrates via chemical vapor deposition (CVD) and atomic layer deposition (ALD) are well established and the deposition processes employed can be used herein to form the silicon and oxide containing films described herein using at least one organoaminosilane precursor having Formula A through C described herein.

The method used to form the dielectric films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). The silicon and oxide containing films may be formed in deposition chambers designed for chemical vapor deposition (CVD), low pressure chemical vapor deposition (LPCVD), plasma enhanced CVD (PECVD), atomic layer deposition (ALD), and so forth. The term CVD as used herein is intended to include each of these processes which are employed in the semiconductor industry. In certain embodiments, the silicon and oxide containing films are deposited via plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits conformal films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the film is deposited using an ALD process. In another embodiment, the film is deposited using a CCVD process. In a further embodiment, the film is deposited using a thermal CVD process.

In certain embodiments, the method disclosed herein avoids pre-reaction of the precursors by using ALD or CVD methods that separate the precursors prior to and/or during the introduction to the reactor. In this connection, deposition techniques such as an ALD or CVD processes are used to deposit the dielectric film. In one embodiment, the film is deposited via an ALD process by exposing the substrate surface alternatively to the one or more the silicon-containing precursor, oxygen source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments of the above processes, a reactor chamber is evacuated and a semiconductor substrate placed therein. Then, one or more silane precursors and an oxidizing source are provided to the reactor chamber under conditions wherein a silicon oxide layer is formed on the semiconductor wafer. These films also may be adjusted for carbon, nitrogen and hydrogen content (sometimes referred to as doping) during the process by the addition of carbon, hydrogen and nitrogen sources. The resulting films produced by the use of the organoaminosilane precursors are often referred to as silicon oxide, silicon oxycarbide, silicon oxynitride and silicon carbooxynitride films.

One class of silicon compound suited for the practice of this invention is an organoaminosilane precursor and it is represented by formula A as follows:

In Formula A, R is selected from a $C_1$-$C_{10}$ linear, branched, cyclic, saturated, or unsaturated alkyl group with or without substituents; a $C_6$-$C_{10}$ aromatic group with or without substituents; or a $C_3$-$C_{10}$ heterocyclic group with or without substituents; $R^1$ is selected from a $C_3$-$C_{10}$ linear, branched, cyclic, saturated, or unsaturated alkyl group with or without substituents; a $C_6$-$C_{10}$ aromatic group with or without substituents; a $C_{3-10}$ heterocyclic aromatic group with or without substituents; a $C_3$-$C_{10}$ heterocyclic group with or without substituents; a hydrogen atom; or a silyl group with substituents; or wherein R and W are combined into a heterocyclic group via formation of single or double carbon-carbon bond or linkage through oxygen or nitrogen atom. Representative groups for R and $R^1$ are alkyl groups and particularly the $C_{2-4}$ alkyl groups, such as ethyl, n-propyl, isopropyl, n-butyl, iso-butyl, sec-butyl, tert-butyl, and cyclic groups such as cyclopropyl, cyclobutyl, cyclopentyl, and cyclohexyl. Illustrative of some of the preferred compounds within this class are represented by the formulas:

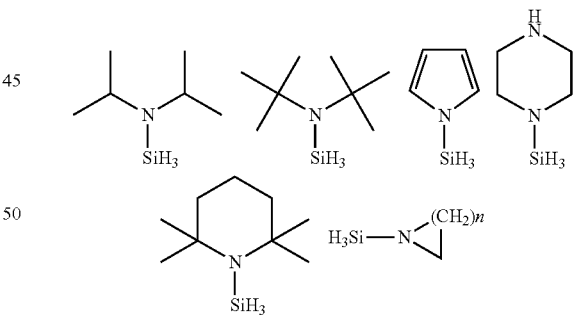

wherein n ranges from 2 to 6 or from 4 to 5. In certain embodiments, R and $R^1$ are the same. In other embodiments, R and $R^1$ are different. In one particular embodiment of the organoaminosilane precursors having Formula A, R is n-propyl and $R^1$ is isopropyl. In another embodiment of the organoaminosilane precursors having Formula A, R is an aromatic group with or without substituents and $R^1$ is a linear or branched alkyl group. In a further embodiment of Formula A, R is a methyl group and $R^1$ is a phenyl group. In yet a further embodiment of Formula A, R is an isopropyl group, $R^1$ is a sec-butyl group and R and $R^1$ are combined to form a 5 or 6 member cyclic group. In yet a further embodiment of Formula A, R and R¹ are combined to form a 5 or 6 member heterocyclic aromatic group including, but no limited to, pyrrole, alkyl substituted pyrrole, imidozale, alkyl substituted imidozale, pyrozale, or an alkyl-substituted pyrozale. In a still further embodiment of Formula A, both R and R¹ are not isobutyl or n-butyl groups.

The second class of organoaminosilane precursor suited for use in producing silicon oxide layers is an organoaminosilane which has two silyl groups pendant from a single nitrogen atom as represented by formula B.

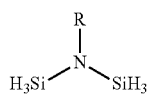

As with the R groups of the Class A compounds, R is selected from the group consisting of $C_2$-$C_{10}$ linear, branched, or cyclic, saturated or unsaturated alkyl groups with or without substituents, a $C_5$-$C_{10}$ aromatic group with or without substituents; an alkylamino group with or without substituents, and a $C_3$-$C_{10}$ heterocyclic group with or without substituents. Specific R groups include methyl, ethyl, propyl, allyl, butyl, dimethylamine group, and cyclic groups such as cyclopropyl, cyclobutyl, cyclopentyl, and cyclohexyl. Illustrative compounds are represented by the formulas:

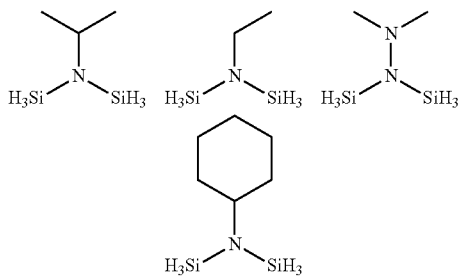

In certain embodiments, R is an aromatic group such as, for example, a phenyl or a benzyl group.

The third class of organoaminosilane compound is represented by formula C.

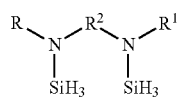

In Formula C, R and R1 are each independently R is selected from a $C_1$-$C_{10}$ linear, branched, cyclic, saturated, or unsaturated alkyl group with or without substituents; a $C_5$-$C_{10}$ aromatic group with or without substituents; or a $C_3$-$C_{10}$ heterocyclic group with or without substituents; R¹ is selected from a $C_3$-$C_{10}$ linear, branched, cyclic, saturated, or unsaturated alkyl group with or without substituents; a $C_5$-$C_{10}$ aromatic group with or without substituents; a $C_{3-10}$ heterocyclic aromatic group with or without substituents; a $C_3$-$C_{10}$ heterocyclic group with or without substituents; a hydrogen atom; or a silyl group with substituents; or wherein R and R¹ are combined into a heterocyclic group via formation of single or double carbon-carbon bond or linkage through oxygen or nitrogen atom. In certain embodiments, R and R¹ are the same. In alternative embodiments, R and R¹ are different. The R² group bridges the nitrogen atoms. In certain embodiments, the R² group is nothing more than a single bond between the nitrogen atoms. In an alternative embodiment, the R² group it may be a bridging group, such as $SiR_2$, $SiH_2$, a chain, a ring, or a $C_3$-$C_{10}$ linear or a $C_3$-$C_{10}$ branched alkyl. In a further embodiment of Formula C, R and R¹ can be linked together. In the later embodiment, R and R¹ in Formula C can be combined into a heterocyclic group via formation of a single or a double carbon-carbon bond or a linkage through oxygen or nitrogen atom.

Specific examples include those represented by the formula C includes but is not limited to:

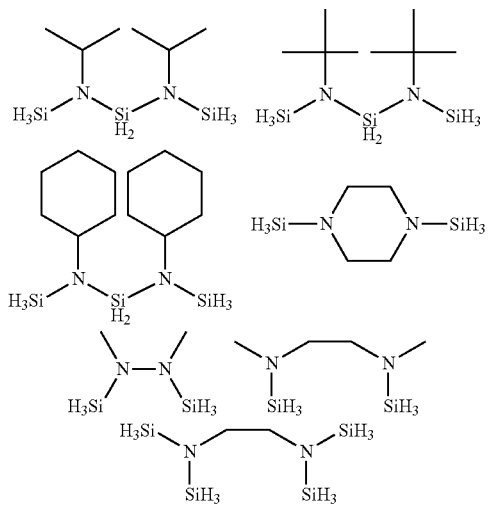

It has been found though that even though the above organoaminosilanes are suitable for producing silicon oxide films on a semiconductor substrate, organoaminosilanes of formula A may be preferred for certain applications. The dialkylaminosilanes described herein may also meet the criteria of some of the prior silanes as precursors in that they form films having similar dielectric constants. In one particular embodiment, the particular organoaminosilane having Formula A diisopropylaminosilane offers excellent low etch rates which offers unexpected properties in the process in that it is stable and has a longer shelf life than many of the other silane precursors.

In Formulas A through C and throughout the description, the term "alkyl" denotes a linear, branched, or cyclic functional group having from 1 to 10, or from 3 to 10, or from 1 to 6 carbon atoms. Exemplary alkyl groups include but are not limited to methyl, ethyl, propyl, isopropyl, butyl, isobutyl, sec-butyl, tert-butyl, pentyl, hexyl, octyl, decyl, dodecyl, tetradecyl, octadecyl, isopentyl, and tert-pentyl.

In Formulas A through C and throughout the description, the term "aryl" denotes a cyclic functional group having from 6 to 12 carbon atoms. Exemplary aryl groups include but are not limited to phenyl, benzyl, tolyl, and o-xylyl.

In Formulas A through C and throughout the description, the term "aromatic" group denotes a functional group having from 3 to 10, from 5 to 10, or 6 to 10 carbon atoms. The term "aromatic group" includes homocyclic or heterocyclic rings which can be substituted with a heteroatom (e.g., O, N, S, halogen atom, etc.), an alkyl group, an alkoxy, and/or an alkyl-amino group. In other embodiments, the aromatic group is not substituted or is unsubstituted. Exemplary aromatic groups include, but are not limited to, pyrrole, alkyl substituted pyrrole, imidozale, alkyl substituted imidozale, pyrozale, or an alkyl-substituted pyrozale. Further exemplary aromatic groups include, but are not limited to, pyrrolidine, alkyl-substituted pyrrolidine, imidazolidine, alkyl substituted imidazolidine, oxazolidine, alkyl substituted oxazolidine, piperidine, alkyl substituted piperidine, morpholine, alkyl substituted morpholine, piperazine, or alkyl substituted piperazine.

In certain embodiments, one or more of the alkyl group, aryl group, and/or alkoxy group may be substituted or with substituents or have one or more atoms or group of atoms substituted in place of a hydrogen atom. Exemplary substituents include, but are not limited to, oxygen, sulfur, phosphorus, halogen atoms (e.g., F, Cl, I, or Br), nitrogen, a $C_1$-$C_{10}$ alkyl group, a $C_1$-$C_{10}$ alkoxy group, and a $C_1$-$C_{10}$ alkyl-amino group. In other embodiments, one or more of the alkyl group, aryl group, alkyl-amino group and/or alkyoxy group is unsubstituted.

In certain embodiments, one or more of the alkyl group and/or aryl group, and/or alkoxy group may be saturated or unsaturated in Formulas A through C. With regard to the term "unsaturated", one or more of the carbon atoms within group can be unsaturated with one or more carbon-carbon double bonds (alkenes) or one or more carbon-carbon triple bonds (alkynes).

The Formula A through Formula C organoaminosilane precursors may be made in a manner described in Applicants' application U.S. Publ. No. 2006/0258173 which is incorporated herein by reference in its entirety.

In certain embodiments, the method described herein further comprises one or more additional silicon-containing precursors other than the organoaminosilane precursor having the above Formulas A through C. Examples of additional silicon-containing precursors include, but are not limited to, organo-silicon compounds such as siloxanes (e.g., hexamethyl disiloxane (HMDSO) and dimethyl siloxane (DMSO)); organosilanes (e.g., methylsilane; dimethylsilane; vinyl trimethylsilane; trimethylsilane; tetramethylsilane; ethylsilane; disilylmethane; 2,4-disilapentane; 1,4-disilabutane; 2,5-disilahexane; 2,2-disilylpropane; 1,3,5-trisilacyclohexane, and fluorinated derivatives of these compounds; phenyl-containing organo-silicon compounds (e.g., dimethylphenylsilane and diphenylmethylsilane); oxygen-containing organo-silicon compounds, e.g., dimethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4,6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5,7,9-pentamethylcyclopentasiloxane; hexamethoxydisiloxane, and fluorinated derivatives of these compounds.

Depending upon the deposition method, in certain embodiments, the one or more silicon-containing precursors may be introduced into the reactor at a predetermined molar volume, or from about 0.1 to about 1000 micromoles. In this or other embodiments, the silicon-containing precursor may be introduced into the reactor for a predetermined time period, or from about 0.001 to about 500 seconds.

As previously mentioned, the dielectric films deposited using the methods described herein are formed in the presence of oxygen using an oxygen source, oxidizing agent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $NO_2$, hydrogen peroxide, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited dielectric film. In a further embodiment, the oxidizing agent to silane precursor ratio is greater than 0.1, preferably from 0.1 to 6 moles oxidizing agent per mole of organoaminosilane precursor.

In certain embodiments, the silicon and oxide film further comprises nitrogen. In this embodiments, an additional gas such as a nitrogen source gas may be introduced into the reactor. Examples of nitrogen source gases may include, for example, NO, $NO_2$, ammonia, ammonia plasma, hydrazine, monoalkylhydrazine, dialkylhydrazine, and combinations thereof.

The deposition methods disclosed herein may involve one or more purge gases. The purge gas, which is used to purge away unconsumed reactants and/or reaction byproducts, is an inert gas that does not react with the precursors. Exemplary inert gases include, but are not limited to, Ar, $N_2$, He, neon, $H_2$ and mixtures thereof. In certain embodiments, a purge gas such as Ar is supplied into the reactor at a flow rate ranging from about 10 to about 2000 sccm for about 0.1 to 1000 seconds, thereby purging the unreacted material such as, but not limited to, one or more precursors, oxygen source, etc. and any byproduct that may remain in the reactor.

In certain embodiments of the method described herein, the temperature of the reactor or a deposition chamber may range from ambient temperature (e.g., 25° C.) to about 700° C. Exemplary reactor temperatures for the ALD or CVD deposition include ranges having any one or more of the following endpoints: 25, 50, 75, 100, 125, 150, 175, 200, 225, 250, 275, 300, 325, 350, 375, 400, 425, 450, 475, 500, 525, 550, 575, 600, 625, 650, 675, or 700° C. Examples of particular reactor temperature ranges include but are not limited to, 25° C. to 375° C., or from 75° C. to 700° C., or from 325° C. to 675° C. In this or other embodiments, the pressure may range from about 0.1 Torr to about 100 Torr or from about 0.1 Torr to about 5 Torr. In one particular embodiment, the dielectric film is deposited using a thermal CVD process at a pressure ranging from 100 mTorr to 600 mTorr. In another particular embodiment, the dielectric film is deposited using an ALD process at a temperature range of 1 Torr or less.

In certain embodiments of the method described herein, the temperature of the substrate in the reactor or a deposition chamber, may range from ambient temperature (e.g., 25° C.) to about 700° C. Exemplary substrate temperatures for the ALD or CVD deposition include ranges having any one or more of the following endpoints: 25, 50, 75, 100, 125, 150, 175, 200, 225, 250, 275, 300, 325, 350, 375, 400, 425, 450, 475, 500, 525, 550, 575, 600, 625, 650, 675, or 700° C. Examples of particular substrate temperature ranges include but are not limited to, 25° C. to 375° C., or from 75° C. to 700° C., or from 325° C. to 675° C. In certain embodiments, the substrate temperature may be the same as or in the same temperature range as the reactor temperature during the deposition. In other embodiments, the substrate temperature differs from the reactor temperature during the deposition.

The respective step of supplying the precursors, the oxygen source, and/or other precursors, source gases, and/or reagents may be performed by changing the time for supplying them to change the stoichiometric composition of the resulting dielectric film.

Energy is applied to the at least one of the precursor, oxygen source, reducing agent, other precursors or combination thereof to induce reaction and to form the dielectric film or coating on the substrate. Such energy can be provided by, but not limited to, thermal, plasma, pulsed plasma, helicon plasma, high density plasma, inductively coupled plasma, X-ray, e-beam, photon, and remote plasma methods. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor. In certain embodiments wherein a plasma is used, the RF power in the plasma chamber may range between 100 W and 1500 W.

The organoaminosilane precursors and/or other precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, leading to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

The Formula A through C aminosilane precursors described herein can further comprise at least one pressurizable vessel fitted with the proper valves and fittings to allow the delivery of one or more precursors or chemical reagents to the process reactor. In certain embodiments, the contents of the vessel(s) can be premixed. Alternatively, the precursors can be maintained in separate vessels or in a single vessel having separation means for maintaining the precursors separate during storage. Such vessels can also have means for mixing the precursors when desired. The precursors can be pre-mixed and then delivered to the reaction chamber, or alternatively, delivered separately wherein the mixture is formed in-situ within the reaction chamber and/or on the deposited film itself.

In one particular embodiment, the silicon-containing film is deposited using a low pressure chemical vapor deposition process. Low pressure chemical vapor deposition processes (LPCVD) involve chemical reactions that are allowed to take place on a variety of substrates, e.g., silicon and aluminum, within a pressure range generally of from 0.1 to 500 torr, preferably from 0.5 to 20 Torr. High pressure CVD may result in gas phase nucleation or predeposition before the desired substrate is reached. Dilution of the silane precursor with inert gases, such as nitrogen and helium, may be required for such high pressure reactions. The use of inert gases by the fabricator to achieve corresponding dilution of the precursor may improve the conformality of the deposition or improve the penetration for chemical vapor infiltration. By using an isopropylaminosilane, and preferably diisopropylaminosilane as a particular silane precursor, one can form an oxide film which deposits at a rate of 5 Å/min to 60 Å/min with refractive index in the range 1.45 to 1.70, and wet etch rate (in 1% HF solution) in the range 0.01 Å/second to 1.5 Å/second.

In a typical ALD or CCVD process, the substrate such as a silicon oxide substrate is heated on a heater stage in a reaction chamber that is exposed to the silicon-containing precursor initially to allow the complex to chemically adsorb onto the surface of the substrate.

A purge gas such as argon purges away unabsorbed excess complex from the process chamber. After sufficient purging, an oxygen source may be introduced into reaction chamber to react with the absorbed surface followed by another gas purge to remove reaction by-products from the chamber. The process cycle can be repeated to achieve the desired film thickness.

In this or other embodiments, it is understood that the steps of the methods described herein may be performed in a variety of orders, may be performed sequentially or concurrently (e.g., during at least a portion of another step), and any combination thereof. The respective step of supplying the precursors and the oxygen source gases may be performed by varying the duration of the time for supplying them to change the stoichiometric composition of the resulting dielectric film.

In another embodiment of the method disclosed herein, the dielectric films is formed using a ALD deposition method that comprises the steps of:

introducing an at least one organoaminosilane precursor represented by the formulas:

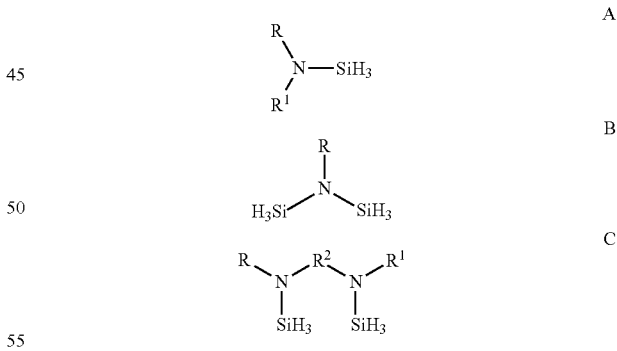

wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a cyclic group comprising from 2 to 6 carbon atoms and $R^2$ representing a single bond, $(CH_2)$, chain, a ring, $SiR_2$, or $SiH_2$; and chemisorbing the at least one organoaminosilane precursor onto a substrate;

purging away the unreacted at least one organoaminosilane precursor using a purge gas;

providing an oxygen source to the organoaminosilane precursor onto the heated substrate to react with the sorbed at least one organoaminosilaneprecursor; and optionally purging away any unreacted oxygen source.

The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting dielectric film, although always using oxygen in less than a stoichiometric amount relative to the available silicon.

For multi-component dielectric films, other precursors such as silicon-containing precursors, nitrogen-containing precursors, reducing agents, or other reagents can be alternately introduced into the reactor chamber. In a further embodiment of the method described herein, the dielectric film is deposited using a thermal CVD process. In this embodiment, the method comprises: placing one or more substrates into a reactor which is heated to a temperature ranging from ambient temperature to about 700° C. and maintained at a pressure of 1 Torr or less; introducing at least one silicon precursor selected from a silicon-containing precursor having the following formula represented by the formulas:

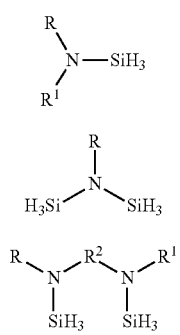

wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a cyclic group comprising from 3 to 10 carbon atoms and $R^2$ representing a single bond, $(CH_2)$, chain, a ring, $C_3$-$C_{10}$ branched alkyl, $SiR_2$, or $SiH_2$, to deposit a dielectric film onto the one or more substrates wherein the reactor is maintained at a pressure ranging from 100 mTorr to 600 mTorr during the introducing step.

In certain embodiments, the resultant dielectric films or coatings can be exposed to a post-deposition treatment such as, but not limited to, a plasma treatment, chemical treatment, ultraviolet light exposure, electron beam exposure, and/or other treatments to affect one or more properties of the film.

The dielectric films described herein have a dielectric constant of 6 or less. Preferably, the films have a dielectric constant of about 5 or below, or about 4 or below, or about 3.5 or below.

As mentioned previously, the method described herein may be used to deposit a dielectric film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited dielectric films have applications, which include, but are not limited to, computer chips, optical devices, magnetic information storages, coatings on a supporting material or substrate, microelectromechanical systems (MEMS), nanoelectromechanical systems, thin film transistor (TFT), and liquid crystal displays (LCD).

The following examples are provided to illustrate various embodiments of the invention and are not intended to restrict the scope thereof.

EXAMPLES

General Procedure

The precursors were tested in an LPCVD reactor used to qualify experimental precursors for silicon oxide depositions. The precursors were degassed and metered into the reactor through a low-pressure mass flow controller (MFC). The MFC flows were calibrated against weight losses of the chemicals vs. time of flow. Additional reactants, such as oxygen, and diluents, such as nitrogen and helium, were also metered into the reactor through calibrated MFCs. The reactor was connected to a roots blower/dry pump combination capable of evacuating the reactor to below 1E-4 Torr (0.013 Pa). The temperature across a load of silicon wafers, during deposition, was within 1° C. of the set point.

The wafers were loaded onto a quartz boat and inserted in the reactor. The reactor is pumped to base pressure and checked for leaks. The system was ramped to the process temperature with gas flows that would dilute any residual oxygen or moisture to prevent any oxidation of the silicon wafers as the reactor heats up. The reactor was then stabilized for a predetermined time to bring all wafer surfaces to an equal temperature as had been determined by previous measurements on wafers with attached thermocouples.

The gases and vapors were injected into the reactor for a predetermined deposition time at a controlled pressure. Next, the gases were shut off, and the reactor pumped to a base pressure. The reactor then was pump-purged, pumped down, and pump-purged to clear any reactive gases and vapors as the reactor was cooled down. The reactor was backfilled to atmospheric pressure; the wafers were removed and allowed to cool to room temperature. The deposited films were then measured for film thickness, film refractive index, film stress, infrared absorbances, dielectric constant, and acid etch rate.

Example 1

Formation of Silicon Oxide Film Using Diethylaminosilane Precursor

The general procedure outlined above was followed using the following reactants and flow conditions. 11.7 sccm of diethylaminosilane (DEAS) was flowed into the LPCVD reactor at 500° C. with 5.9 sccm $O_2$ at 0.6 Torr for a deposition time of 74 minutes.

The average film thickness of the silicon oxide film was 123 nm and refractive index was 1.459. The wet etch rate of this film in 1% HF solution was 1.38 Å/second. The infrared spectra were dominated by Si—O—Si absorptions. C—H absorptions were in the noise, indicating the film was silicon dioxide. Film composition analysis by Rutherford backscattering spectroscopy (hydrogen by forward scattering) indicated that this film was 28 atom percent silicon, 57 atom percent oxygen, 11 atom percent hydrogen, 3 atom percent carbon, and 1 atom percent nitrogen, indicating that the film was silicon dioxide with hydrogen, carbon, and nitrogen impurities.

Example 2

Formation of Silicon Oxide Film Using Diethylaminosilane Precursor

The procedure of Example 1 was followed with the exception of process conditions. The purpose was to determine the effect of a higher temperature and reduced reaction time. In this example, 11.7 sccm of diethylaminosilane (DEAS) was flowed into a reactor at 600° C. with 5.9 sccm $O_2$ at 0.6 Torr for a deposition time of 33 minutes.

The average film thickness of the silicon oxide film was 157 nm and the refractive index was 1.501. The wet etch rate of this film in 1% HF solution was 0.41 Å/second. The infrared spectra were dominated by Si—O—Si absorptions. C—H absorptions were in the noise, indicating the film was silicon oxide. Film composition analysis by Rutherford backscattering spectroscopy (hydrogen by forward scattering) indicated that this film was 27 atom percent silicon, 47 atom percent oxygen, 15 atom percent hydrogen, 7 atom percent carbon, and 4 atom percent nitrogen, indicating that the film was silicon dioxide with hydrogen, carbon, and nitrogen impurities.

Example 3

Formation of Silicon Oxide Film Using Diisopropylaminosilane Precursor

The procedure of Example 1 was followed essentially with the exception of process conditions and the precursor. In this example, 10.5 sccm of diisopropylaminosilane (DIPAS) was flowed into a reactor at 500° C. with 5.0 sccm $O_2$ at 0.6 Torr for a deposition time of 74 minutes.

The average film thickness of the silicon oxide film was 112 nm and refractive index was 1.458. The wet etch rate of this film in 1% HF solution was 1.39 Å/second. The infrared spectra were dominated by Si—O—Si absorptions. C—H absorptions were in the noise, indicating the film was silicon oxide. Film composition analysis by Rutherford backscattering spectroscopy (hydrogen by forward scattering) indicated that this film was 28 atom percent silicon, 55 atom percent oxygen, 12 atom percent hydrogen, 3 atom percent carbon, and 2 atom percent nitrogen, indicating that the film was silicon dioxide with hydrogen, carbon, and nitrogen impurities.

Example 4

Formation of Silicon Oxide Film Using Diisopropylaminosilane Precursor

The procedure of Example 2 was followed with the exception of process conditions and the precursor. In this example, 10.5 sccm of diisopropylaminosilane (DIPAS) was flowed into a reactor at 600° C. with 5.0 sccm $O_2$ at 0.6 Torr for a deposition time of 33 minutes.

The average film thickness of the silicon oxide film was 124 nm and refractive index was 1.495. The wet etch rate of this film in 1% HF solution was 0.42 Å/second. The infrared spectra were dominated by Si—O—Si absorptions. C—H absorptions were in the noise, indicating the film was silicon oxide. Film composition analysis by Rutherford backscattering spectroscopy (hydrogen by forward scattering) indicated that this film was 28 atom percent silicon, 51 atom percent oxygen, 11 atom percent hydrogen, 6 atom percent carbon, and 4 atom percent nitrogen, indicating that the film was silicon dioxide with hydrogen, carbon, and nitrogen impurities.

In summary, Examples 1 through 4 show that an organoaminosilane of the type set forth in formula A may be used as a precursor for producing silicon oxide films on a semiconductor substrate. The diisopropylaminosilane, DIPAS, offers advantages to the use of diethylaminosilane (DEAS) as a precursor in a low etch rate oxide process. DEAS is less stable than DIPAS at room temperature. The instability of DEAS can result in many EH&S management, production, supply line (including warehousing and shipping), and end user process challenges. Examples 3 and 4 show the oxide films formed from DIPAS generally have the same etch rates, dielectric constants, refractive index, and qualitative composition (via FTIR) as the oxide films formed from DEAS in Examples 1 and 2 under similar process conditions. Thus, from both chemical and process viewpoints, DIPAS is a preferred precursor for producing low etch rate silicon oxide films.

Example 5

Atomic Layer Deposition of Silicon Oxide Films

ALD depositions using various organoaminosilane precursors in the monoaminosilane and bisaminosilane classifications as comparatives and the results of the depositions are provided in Table II. Attempts to deposit the bisaminosilanes bis(di-sec-butylamino)silane and bis(di-n-butylamino)silane and the trisaminosilane tris-(di-n-butylamino)silane were unsuccessful because the vapor pressure of these precursors was too low for precursor delivery. The depositions were performed on a laboratory scale ALD processing tool at either 150° C. or 300° C. for either 500 or 1,000 process cycles with ozone as the oxygen source gas (see Table II for temperature and number of process cycles). The resultant $SiO_2$ films were characterized for deposition rate, wet etch rate, refractive index, and % non-uniformity and the results are also provided in Table II. The process steps that were used to deposit the SiO$_2$ films are shown in the following Table I.

TABLE I

Process for Generating Basic ALD Oxide Films with O$_3$

| Step 1 | 6 sec | Nitrogen Purge of Reactor | Flow 1.5 slpm N2 | Purges out unreacted chemical from reactor |
|---|---|---|---|---|
| Step 2 | 6 sec | Chamber evacuation | <100 mT | Preps the reactor for the precursor dose |
| Step 3 | 2 sec | Close throttle valve | | Increases precursor resonance time |
| Step 4 | variable | Dose Organoaminosilane Precursor | | Reactor pressure typically <1 T during dose |
| Step 5 | 6 sec | Nitrogen Purge of Reactor | Flow 1.5 slpm N2 | Purges out unreacted chemical from reactor |
| Step 6 | 6 sec | Chamber evacuation | <100 mT | Preps the reactor for the precursor dose |
| Step 7 | 2 sec | Close throttle valve | | Increases precursor resonance time |
| Step 8 | 2 sec | Dose Ozone | | O$_3$ at 15-17% post generator, P =< 8 T |

The resultant SiO$_2$ films were characterized for deposition rate, wet etch rate, refractive index, and % non-uniformity and the results are also provided in Table II. In Table II, the refractive index of the films was measured using a FilmTek 2000SE ellipsometer by fitting the reflection data from the film to a pre-set physical model (e.g., the Lorentz Oscillator model). For refractive index, a value of around 1.44 to 1.47 would reflect a typical CVD silicon oxide film. All of the precursors tested deposited films having a refractive index of ranging from about 1.4 to about 1.5. The % non-uniformity quoted was obtained from a 9-point map using the standard equation: % non-uniformity=((max−min)/(2*mean)).

In Table II, the wet etch test of silicon oxide films or WER was performed using a 1% HF solution. Thermal oxide wafers were used as reference for the etch test. The films, along with the comparative silicon oxide films, are measured for their thickness at 9 different points across the film surface before and after etch using an ellipsometer. The etch rate is then calculated as the thickness reduction divided by the time that the films are immersed into the HF solution.

For the precursors containing the substituent diisopropyl, the results in Table II show that the monoaminosilane precursor or DIPAS had a significantly greater deposition rate compared to the bisaminosilane precursor or BisDIPAS. A higher deposition rate is a desired property for the semiconductor industry. Thus, for precursors having the same substituent diisopropyl, the higher deposition rate indicates that precursors having the SiH$_3$ group are more reactive than the precursors having the SiH$_2$ group.

For the precursors containing the substituent diisopropyl, the results in Table II also show that the monoaminosilane precursor or DIPAS had a lower % non-uniformity compared to the bisaminosilane precursor or BisDIPAS. Lower % non-uniformity is a desired property for the semiconductor industry.

The characterization of the chemical composition of the films deposited using various precursors or film nos. 2 and 4 deposited from DIPAS, film nos. 9 and 10 deposited from BisDIPAS, film no. 12 deposited from DSBAS, and film no. 17 deposited from DNBAS was performed using a Physical Electronics 5000VersaProbe XPS Spectrometer, which is equipped with multi-channel plate detectors (MCD) and an Al monochromatic X-ray source and the results are presented in Table III. The XPS data shows that the films deposited from the various aminosilane precursors had comparable film composition, with no gross C or N contamination.

Figure 1B:
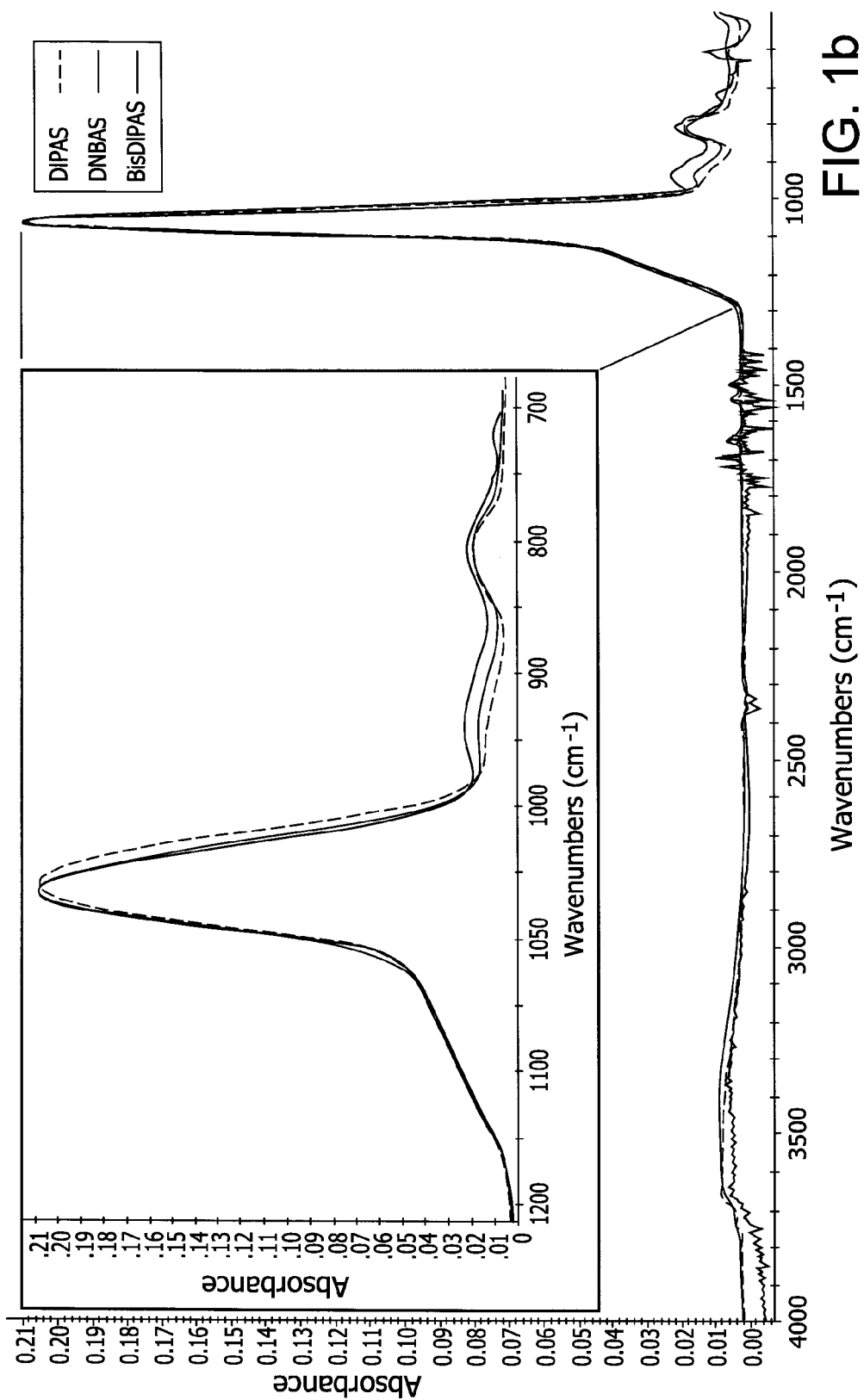

FTIR data was obtained for silicon dioxide films deposited from the precursors DIPAS (film Nos. 5 and 6), BisDIPAS (film Nos. 7 and 8) and DNBAS (film Nos. 16 and 18) and the results of this data are provided in FIGS. 1a (150° C. depositions) and 1b (300° C. depositions). FTIR data was collected on the films using a Thermo Nicolet Nexus 470 system equipped with a DTGS KBR detector and KBr beam splitter. The FTIR spectra in FIGS. 1A and 1B support the XPS data, indicating that all films produced are of similar silicon oxide structure.

Additional film characterization was conducted on DIPAS film no. 2, 98 (BisDIPAS film no. 12), DSBAS film no. 12, and DNBAS film no. 17 via secondary ion mass spectrometry (SIMS). The SIMS data established that the films deposited from the various aminosilane precursors had comparable film composition, with no gross C or N contamination which confirms the XPS shown in Table III and FTIR data shown in FIGS. 1A and 1B.

TABLE II

ALD Deposition Results

| Film No. | Precursor | Deposition Rate (Å/cycle) | Wet Etch Rate (Å/min.) | Refractive Index | % Non-Uniformity |
|---|---|---|---|---|---|
| 1 | DIPAS 150° C./500 cycles | 1.576 | 306.00 | 1.4503 | 1.33 |
| 2 | DIPAS 150° C./1000 cycles | 1.825 | 294.00 | 1.4587 | 0.82 |
| 3 | DIPAS 300° C./500 cycles | 1.582 | 372.00 | 1.4355 | 1.07 |
| 4 | DIPAS 300° C./1000 cycles | 1.881 | 322.20 | 1.4480 | 0.64 |
| 5 | DIPAS 150° C./500 cycles | 1.508 | 330.00 | 1.4663 | 0.93 |
| 6 | DIPAS 300° C./500 cycles | 1.605 | 434.00 | 1.4411 | 0.62 |
| 7 | BisDIPAS 300° C./500 cycles | 0.469 | 364.20 | 1.4985 | 2.56 |
| 8 | BisDIPAS 150° C./500 cycles | 0.181 | 312.00 | 1.5161 | 11.60 |
| 9 | BisDIPAS 300° C./1000 cycles | 0.827 | 352.20 | 1.4490 | 1.93 |
| 10 | BisDIPAS 150° C./1000 cycles | 0.243 | 316.20 | 1.5178 | 10.27 |
| 11 | DSBAS 150° C./500 cycles | 1.206 | 306.00 | 1.4349 | 2.40 |
| 12 | DSBAS 150° C./1000 cycles | 1.619 | 286.20 | 1.4332 | 1.36 |
| 13 | DSBAS 300° C./500 cycles | 1.142 | 328.20 | 1.4353 | 3.15 |
| 14 | DSBAS 300° C./1000 cycles | 1.585 | 318.00 | 1.4513 | 1.04 |
| 16 | DNBAS 150° C./500 cycles | 1.681 | 265.80 | 1.4524 | 1.07 |
| 17 | DNBAS 150° C./1000 cycles | 1.848 | 271.80 | 1.4576 | 0.87 |
| 18 | DNBAS 300° C./500 cycles | 1.374 | 355.80 | 1.4580 | 1.24 |
| 19 | DNBAS 300° C./1000 cycles | 1.860 | 322.20 | 1.4580 | 0.73 |

TABLE III

Atomic composition for silicon oxide films deposited by ALD from various aminosilane precursors.

| Film No. | Precursor | C 1s | O 1s | Si 2p | N 1s |
|---|---|---|---|---|---|
| 12 | (Di-secbutylamino)silane 150° C./1000 cycles | — | 67.6 | 32.4 | — |
| 2 | (Di-isopropylamino)silane 150° C./1000 cycles | — | 68.1 | 31.9 | — |
| 4 | (Di-isopropylamino)silane 300° C./1000 cycles | — | 67.5 | 32.5 | — |
| 17 | (Di-n-butylamino)silane 150° C./1000 cycles | — | 68.0 | 32.0 | — |
| 10 | Bis(Di-isopropylamino)silane 150° C./1000 cycles | — | 68.0 | 32.0 | — |
| 9 | Bis(Di-isopropylamino)silane 300° C./1000 cycles | — | 68.0 | 32.0 | — |

Example 6

Comparison of Deposition and Resultant Silicon Oxide Films for Formula A (DIPAS), Formula B (N-(2-Pyridino)disilazane), and Formula C (7,9-disilyl-7,9-diaza-8-sila-bicyclo[4,3,0]nonane) Precursors The general procedure outlined above for LPCVD of silicon oxide films in Example 1 was followed using the reactants and flow conditions provided in Table IV. The deposited silicon oxide films were then evaluated and the results of the evaluations are also provided in Table IV. For each of the films, the wet etch rate was determined using a 1:99 HF/H20 solution, or 1 part 49% HF to 99 parts water and was compared to a thermal oxide WER of 0.5 Å/second. The wet etch rate was compared to a thermal baseline film to verify the acid concentration and an equivalent WER for each test.

For the Formula B precursor or N-(2-Pyridino)disilazane, the average film thickness of the silicon oxide film was 4586 Å and refractive index was 1.5696. The deposition rate was approximately 51 Å per minute. The wet etch rate of this film in a 1:99 HF/H20 solution, or 1 part 49% HF to 99 parts water, was 24 Å/second compared to a thermal oxide WER of 0.5 Å/second. By comparison, the Formula A precursor or diisopropylaminosilane (DIPAS) had a WER of approximately 3 Å/min and the formula C precursor having the chemical name 7,9-disilyl-7,9-diaza-8-sila-bicyclo[4,3,0]nonane, had a WER of 0.8 Å/min.

For the Formula B and Formula C precursors, the infrared spectra were dominated by Si—O—Si absorptions. C—H absorptions were in the noise, indicating the film was silicon oxide. Film composition analysis by X-ray Photospectroscopy (XPS) indicated that this film was 30.6 atom percent silicon, 51.3 atom percent oxygen, 12.5 atom percent carbon, and 5.6 atom percent nitrogen, indicating that the film was silicon dioxide with carbon and nitrogen impurities.

TABLE IV

| | Precursor Formula A (DIPAS) | Precursor Formula B | Precursor Formula C |
|---|---|---|---|
| Precursor Flow (sccms) | 11.2 | 13.7 | 15 |
| Oxygen flow (sccms) | 20 | 20 | 20 |
| Reactor Temperature (° C.) | 475 | 475 | 550 |
| Reactor Pressure (mTorr) | 250 | 250 | 250 |
| Deposition time (minutes) | 180 | 90 | 60 |
| Deposition rate (Å/min) | 12 | 51 | 25 |
| Refractive Index | 1.4589 | 1.5696 | 1.5687 |
| WER in 1:99 HF:H$_2$O (Å/sec) | 2.3 | 25 | 0.9 |
| XPS O 1s | 67.5 | 51.3 | 51.5 |
| XPS Si 2p | 32.5 | 30.6 | 32.1 |
| XPS C 1s | ND | 12.5 | 9.6 |
| XPS N 1s | ND | 5.6 | 6.9 |

Example 7

Atomic Layer Deposition of Silicon Oxide Films Using Formula B precursors Diphenyldisilazane and N-(2-Pyridino)disilazane)

ALD depositions of silicon oxide films using two Formula B organoaminosilanes or diphenyldisilazane and N-(2-Pyridino)disilazane) and ozone were conducted and the results of these depositions are provided in Table V. The process steps that were used to deposit the SiO$_2$ films were similar to that in Table I of Example 5. The depositions were performed on a laboratory scale ALD processing tool at either 150° C. or 300° C. for either 500 or 1,000 process cycles with ozone as the oxygen source gas (see Table V for deposition temperature and number of process cycles). The resultant SiO$_2$ films were characterized for deposition rate, refractive index, and % non-uniformity in the manner described in Example 5 and the results of the characterizations are also provided in Table V.

TABLE V

ALD Deposition Results

| Organoaminosilane Precursor | Deposition Rate (Å/cycle) | Refractive Index | % Non-Uniformity |
|---|---|---|---|
| N-Phenyldisilazane 150° C./500 cycles | 0.132 | 1.7242 | 21.32 |
| N-Phenyldisilazane 300° C./500 cycles | 0.216 | 1.5293 | 12.98 |
| N-(2-Pyridino)disilazane) (1 second Dose) 300° C./500 cycles | 1.5 | 1.4562 | 1.13 |
| N-(2-Pyridino)disilazane) (2 seconds Dose) 300° C./500 cycles | 1.656 | 1.4558 | 0.65 |

The invention claimed is:

1. A method for forming a silicon oxide film on a substrate via a vapor deposition process, the method comprising:
   introducing an organoaminosilane represented by the formulas:

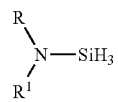

A

-continued

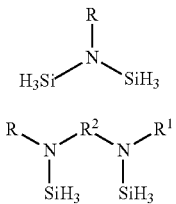

wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a cyclic group comprising from 2 to 6 carbon atoms and $R^2$ representing a single bond, ($CH_2$), chain, a ring, $C_3$-$C_{10}$ branched alkyl, $SiR_2$, or $SiH_2$ into a deposition chamber;
introducing at least one oxidizing agent into the deposition chamber wherein the at least one oxidizing agent reacts with the organoaminosilane to provide the silicon oxide film on the substrate
wherein the vapor deposition process is at least one selected from the group consisting of at least one selected from chemical vapor deposition, low pressure vapor deposition, plasma enhanced chemical vapor deposition, cyclic chemical vapor deposition, plasma enhanced cyclic chemical vapor deposition, atomic layer deposition, and plasma enhanced atomic layer deposition, and
wherein the vapor deposition process is conducted at one or more temperatures ranging from 25° C. to 375° C.

2. The method of claim 1 wherein the vapor deposition process comprises a plasma.

3. The method of claim 2 wherein the plasma is directly generated in the deposition chamber.

4. The method of claim 2 wherein the plasma is generated outside of the deposition chamber and supplied into the deposition chamber.

5. A composition for depositing a silicon-containing film by a vapor deposition process, the composition comprising:
an organoaminosilane precursor represented by the following formula A:

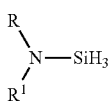

wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents and $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a cyclic group;

a gas selected from the group consisting of an inert gas and nitrogen.

6. The composition of claim 5 wherein R and $R^1$ in Formula A are each independently selected from the group consisting of isopropyl, t-butyl, sec-butyl, t-pentyl, and sec-pentyl groups.

7. The composition of claim 6 wherein R and $R^1$ in Formula A are each isopropyl.

8. The composition of claim 6 wherein R and $R^1$ in Formula A are each sec-butyl.

9. The composition of claim 5 wherein R and $R^1$ in Formula A are combined into a cyclic group.

10. A composition for depositing a silicon-containing film in a vapor deposition process, the composition comprising:
an organoaminosilane precursor represented by the following formula; and

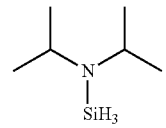

a gas selected from the group consisting of an inert gas and nitrogen.

11. The composition of claim 10 wherein the gas comprises the inert gas.

12. The composition of claim 11 wherein the inert gas comprises helium.

13. The composition of claim 10 wherein the composition is contained in a pressurizable vessel fitted with the proper valves and fittings to allow delivery of to the process reactor.

14. A precursor formulation comprising:
an organoaminosilane represented by the formulae:

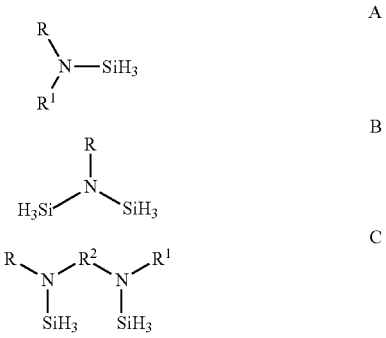

wherein R is selected from a $C_1$-$C_{10}$ linear, branched, or cyclic, saturated or unsaturated alkyl group with or without substituents; a $C_5$-$C_{10}$ aromatic group with or without substituents, a $C_3$-$C_{10}$ heterocyclic group with or without substituents, or a silyl group in formula C with or without substituents, $R^1$ is selected from a $C_3$-$C_{10}$ linear, branched, cyclic, saturated or unsaturated alkyl group with or without substituents; a $C_5$-$C_{10}$ aromatic group with or without substituents, a $C_3$-$C_{10}$ heterocyclic group with or without substituents, a hydrogen atom, a silyl group with substituents and wherein R and $R^1$ in formula A also being combinable into a cyclic group comprising from 2 to 6 carbon atoms and $R^2$ representing a single bond, ($CH_2$), chain, a ring, $C_3$-$C_{10}$ branched alkyl, $SiR_2$, or $SiH_2$ into a deposition chamber; and a solvent.

* * * * *